(12) United States Patent
Osada et al.

(10) Patent No.: US 8,901,044 B2
(45) Date of Patent: *Dec. 2, 2014

(54) METHOD TO PREPARE MAGNETIC BEADS CONJUGATED WITH SMALL COMPOUNDS

(75) Inventors: Hiroyuki Osada, Saitama (JP); Kaori Honda, Saitama (JP); Kunihiro Ohta, Tokyo (JP); Akiho Murayama, Tokyo (JP)

(73) Assignee: Riken, Wako-Shi (JP)

( * ) Notice: Subject to any disclaimer, the term of this patent is extended or adjusted under 35 U.S.C. 154(b) by 345 days.

This patent is subject to a terminal disclaimer.

(21) Appl. No.: 12/777,562

(22) Filed: May 11, 2010

(65) Prior Publication Data

US 2010/0311608 A1 Dec. 9, 2010

Related U.S. Application Data

(60) Provisional application No. 61/262,188, filed on Nov. 18, 2009.

(30) Foreign Application Priority Data

May 13, 2009 (JP) ................. 2009-116325

(51) Int. Cl.
*C40B 30/04* (2006.01)
*B05D 3/06* (2006.01)
*C40B 40/00* (2006.01)
*G01N 33/543* (2006.01)
*B03C 1/01* (2006.01)

(52) U.S. Cl.
CPC ............ *G01N 33/54326* (2013.01); *B03C 1/01* (2013.01); *G01N 33/54353* (2013.01); *B03C 2201/18* (2013.01)
USPC .......................................................... 506/9

(58) Field of Classification Search
CPC ........... C40B 30/04; C40B 40/00; B05D 3/06
USPC .......................................................... 506/9
See application file for complete search history.

(56) References Cited

U.S. PATENT DOCUMENTS

| 6,001,579 | A | * | 12/1999 | Still et al. ........................ 506/28 |
| 7,329,496 | B2 | * | 2/2008 | Dower et al. ................ 435/6.11 |
| 7,713,706 | B2 | * | 5/2010 | Osada et al. .................... 435/7.1 |
| 2003/0119021 | A1 | * | 6/2003 | Koster et al. ....................... 435/6 |
| 2004/0209282 | A1 | * | 10/2004 | Ault-Riche et al. .............. 435/6 |
| 2006/0183225 | A1 | | 8/2006 | Ohta et al. |
| 2006/0194251 | A1 | | 8/2006 | Osada et al. |
| 2008/0227653 | A1 | * | 9/2008 | Fodor et al. ....................... 506/9 |

FOREIGN PATENT DOCUMENTS

| JP | 2004309372 | | * 11/2004 |
| JP | 2005221394 | A | 8/2005 |
| JP | 3901120 | | 4/2007 |
| JP | 2007139587 | A | 6/2007 |
| WO | 2007076132 | A2 | 7/2007 |

OTHER PUBLICATIONS

Please note that Japanese document can be found in U.S. Appl. No. 10/551,809.*
Penchovsky et al (Nucleic Acid, 2000, 22, e98).*
http://www.riken.jp/law-www/bioarchitect/report/2007/07-G/07_G26_ohta%20.pdf, 2007.*
First Office Action in corresponding Japanese application No. 2010-110952, dated Oct. 17, 2013.
Kanoh, et al. "Photo-Cross-Linked Small-Molecule Affinity Matrix for Facilitating Forward and Reverse Chemical Genetics." 2005 Wiley-VCH Verlag GmbH & Co. KGaA, Weinheim, Angew. Chem. 2005, 117, 3625-3628.
Kanoh, et al. "Photo-Cross-Linked Small-Molecule Affinity Matrix for Facilitating Forward and Reverse Chemical Genetics—Supporting Information." 2005 Wiley-VCH Verlag GmbH & Co. KGaA, Weinheim, Angew. Chem. 2005.
Kawatani, et al. "The identification of an osteoclastogenesis inhibitor through the inhibition of glyoxalase I." 2008 The National Academy of Sciences of the USA. PNAS Aug. 19, 2008 vol. 105 No. 33 11691-11696.
Kawatani, et al. "The identification of an osteoclastogenesis inhibitor through the inhibition of glyoxalase I—Supporting Informafion." 2008 The National Academy of Sciences of the USA.
Seo et al., Nature Biotech. 23: 731-735, 2005.

* cited by examiner

*Primary Examiner* — Maria Leavitt
*Assistant Examiner* — Amy M Bunker
(74) *Attorney, Agent, or Firm* — Pearne & Gordon LLP (57) ABSTRACT

It is an object of the present invention to provide a method for stably and efficiently binding a compound to magnetic beads. The present invention relates to a method for producing compound-bound magnetic beads, which comprises: allowing a compound to come into contact with magnetic beads, on the surface of each of which a photoreactive compound has bound; extending the magnetic beads together with the compound on a support; and applying light to the magnetic beads to form a covalent bond between the photoreactive compound and the compound.

8 Claims, 7 Drawing Sheets

METHOD TO PREPARE MAGNETIC BEADS CONJUGATED WITH SMALL COMPOUNDS

REFERENCE FOR RELATED APPLICATIONS

The present application claims priority from Japanese Patent Application No. 2009-116325, filed on May 13, 2009, and from Provisional U.S. Patent Application No. 61/262,188, filed on Nov. 18, 2009; the disclosures of which are hereby incorporated by reference in their entirety.

BACKGROUND OF THE INVENTION

1. Field of the Invention

The present invention relates to a method for immobilizing a compound on magnetic beads.

2. Description of the Related Art

Magnetic beads are extremely useful for obtaining a product of interest, such as a protein, a DNA, or a cell, from a mixture of various substances. For example, when a specific protein is obtained from a cell extract, a ligand that specifically binds to a protein of interest is immobilized on the surface of each of magnetic beads. The thus ligand-immobilized magnetic beads are then added to the extract, and the protein of interest is allowed to bind to the magnetic beads via the ligand. Thereafter, the magnetic beads are recovered utilizing magnetic force and the like, thereby obtaining the protein of interest. Hence, if taking advantage of the characteristics of magnetic beads, a substance of interest can be efficiently obtained from a mixture comprising various substances.

Among biological substances, in a case in which an antibody having a desired specificity is selected from an antibody library, the use of magnetic beads is particularly effective. For example, in a case in which a protein is used as an antigen and in which an antibody specifically binding to such antigen is selected from a library, if magnetic beads on the surface of each of which a tosyl group or an epoxy group is present are used, covalent bonds can be formed between such functional groups and many free amino groups existing in the protein. Thus, the antigenic protein can be easily immobilized on the magnetic beads. However, in the case of a compound having almost no amino groups (for example, a low-molecular-weight compound such as a lipid), since it is difficult to bind the compound to the magnetic beads mediated by such amino groups, other methods should have been applied. Examples of such other methods attempted to replace the above-mentioned method include: a method mediated by a carrier protein; a method utilizing a biotin-avidin bond involving biotinylation; a method using magnetic beads having hydrophobic functional groups; a method of artificially introducing an amino group into an antigen and a method using a photoreactive crosslinking reagent (US2006194251). However, the use of the method of binding a carrier protein to an antigen, the method of biotinylating an antigen, or the like, has been problematic in that these methods may affect the steric structure of an antigenic molecule, or in that an antibody may be obtained selectively with respect to such biotinylated portion or carrier protein. Moreover, if the method using magnetic beads having hydrophobic functional groups is applied to the selection of an antibody from an antibody library constituted with living cells (see, for example, an antibody library prepared by an ADLib method, US20060183225; Seo et al, Nature Biotech. 23: 731-735, 2005), antigens are easily released from the beads, and the thus released antigens have lethal effects on the cells constituting the library. Furthermore, since the method of artificially introducing amino groups into antigens and then directly binding the antigens to magnetic beads has required a chemical synthesis comprising complicated steps, this method has required enormous time and expense.

In contrast to the above-described methods, a method of allowing antigens to bind to magnetic beads using a photoreactive crosslinking reagent (a photoreactive compound) has been expected to be an effective, versatile means for immobilizing various types of compounds on magnetic beads. However, as a matter of fact, the efficiency of immobilizing antigens on magnetic beads has been significantly low, under conditions for binding the antigens to the conventionally used solid phase or agarose beads (for example, under ultraviolet irradiation and/or crosslinking conditions). As a result, the expected effects could not be obtained.

Under the above-mentioned circumstances, using magnetic beads, in order to select from an antibody library, an antibody reacting with an antigen which has been hardly immobilized on magnetic beads by the conventional method, it has been necessary to establish a modified method for stably and efficiently immobilizing a compound serving as an antigen on magnetic beads.

SUMMARY OF THE INVENTION

It is an object of the present invention to provide a method for stably and efficiently binding a compound to magnetic beads. Specifically, it is an object of the present invention to provide a method for stably and efficiently binding a compound having almost no amino groups, among various compounds, to magnetic beads.

Under the above-mentioned circumstances, the present inventors have conducted intensive studies. As a result, the inventors have found that a compound is allowed to react with magnetic beads that have been extended at a low density (concentration), so that the molecules thereof can be stably and efficiently bound to the magnetic beads, thereby completing the present invention. Conventionally, in many cases, light had been applied to a mixture consisting of photoreactive compound-bound magnetic beads and a compound in an Eppendorf tube or in a test tube. According to such method, however, the rate of immobilizing a compound on magnetic beads had been low, and thus, this had not been a practical method. Hence, the present inventors have made a hypothesis that, since the applied light was absorbed by the magnetic beads according to the above-described method, the rate of immobilizing the compound would become significantly low. In order to improve this point, the inventors have taken a process of trial and error. As a result, the inventors have solved the aforementioned problem of the conventional method, thereby completing the present invention. According to the present invention, as described in the examples later, the rate of immobilizing a compound on magnetic beads, which is significantly higher than that of the conventional method, can be realized.

Specifically, the main aspects of the present invention relate to the following (1) to (9):

(1) A first aspect of the present invention relates to "a method for producing compound-bound magnetic beads, which comprises: allowing a compound to come into contact with magnetic beads, on the surface of each of which a photoreactive compound has bound; extending the magnetic beads together with the compound on a support; and applying light to the magnetic beads to form a covalent bond between the photoreactive compound and the compound."

(2) A second aspect of the present invention relates to "the method according to (1) above, wherein the magnetic beads are dried, before applying light thereto."
(3) A third aspect of the present invention relates to "the method according to (1) or (2) above, wherein the density of the extended magnetic beads is $1\times10^8$ beads/cm$^2$ or less."
(4) A fourth aspect of the present invention relates to "the method according to any one of (1) to (3) above, wherein the compound has no or almost no amino groups."
(5) A fifth aspect of the present invention relates to "the method according to (4) above, wherein the compound is a lipid."
(6) A sixth aspect of the present invention relates to "magnetic beads produced by the method according to any one of (1) to (5) above."
(7) A seventh aspect of the present invention relates to "a kit comprising magnetic beads and an instruction manual, which is used for the method according to any one of (1) to (5) above."
(8) An eighth aspect of the present invention relates to "the kit according to (7) above further comprising a photoreactive compound and/or a compound."
(9) A ninth aspect of the present invention relates to "a method for selecting an antibody binding to the above-described compound from an antibody library, using the magnetic beads according to (6) above."

EFFECTS OF THE INVENTION

According to the present invention, any given compound can be stably and efficiently bound to magnetic beads.

According to the present invention, a compound having no amino groups can also be stably and efficiently bound to magnetic beads.

According to the present invention, a compound serving as an antigen can be reliably bound to magnetic beads. Thus, such compound-bound magnetic beads can be used to select an antibody of interest from an antibody library comprising living cells, without causing side effects (e.g. a fetal influence on the cells).

According to the present invention, the above-mentioned compound can be bound to magnetic beads at a low cost.

DETAILED DESCRIPTION OF THE PREFERRED EMBODIMENTS

The embodiment of the present invention includes a method for producing compound-bound magnetic beads, which comprises: allowing a compound to come into contact with magnetic beads, on the surface of each of which a photoreactive compound has bound; extending the magnetic beads together with the compound on a support; and applying light to the magnetic beads to form a covalent bond between the photoreactive compound and the compound.

The compound used as a target of the present invention is not particularly limited. Examples of such compound include organic compounds containing carbon, hydrogen, oxygen, nitrogen, sulfur and the like. More specific examples include biomolecules such as a protein, a peptide, a carbohydrate, a lipid and a nucleic acid, and low-molecular-weight organic compounds, and preferably, low-molecular-weight compounds having a relatively low molecular weight. Moreover, the compound used as a target of the present invention also includes compounds having no or almost no amino groups. The type of such compound having almost no amino groups is not particularly limited. For example, it is a compound in which the number of amino groups per molecule is 0 to 5, preferably 0 to 3, and more preferably 0 or 1.

The type of the "photoreactive compound" used in the present invention is not particularly limited, as long as it is activated by the application of light and it formed a covalent bond with any given compound. Examples of such photoreactive compound include: compounds generating nitrene (for example, compounds having an azido group, such as an aromatic azide, an alkyl azide, or a heterocyclic azide); compounds generating carbene (for example, compounds having a diazo group or diazirine ring); compound generating a radical (for example, benzophenones, conjugated ketones such as enones, aromatic halogen compounds, and olefins); compounds generating a carbon electrophile (for example, aromatic diazonium); and compounds comprising a diazonium group, an azido group, a diazirine ring, or a diazo group. In addition, the photoreactive compounds described in Japanese Patent No. 3901120 can also be preferably used. More specifically, a polyethylene glycol linker having a photoaffinity group, N-(17-amino-3,6,9,12,15-pentaoxaheptadecacil)-4-(3-trifluoromethyl-3H-diazirin-yl)-benzamide, and the like can be used.

The "magnetic beads" used in the present invention are not particularly limited, as long as a photoreactive compound can be directly or indirectly bound to each surface thereof. For example, there can be used magnetic beads, the surface of each of which is coated with a polymer such as a polycation, so that an amino group, a carboxyl group, a hydroxy group, or the like can be introduced into the surface. As such magnetic beads, commercially available products may also be used. For example, M450-Epoxy (Dynal), M450-Tosyl (Dynal), and µMACS (Miltenyi) are available. Moreover, persons skilled in the art could readily select a method for binding a photoreactive compound to magnetic beads. Before the reaction with a compound to be reacted with the magnetic beads, such photoreactive compound-bound magnetic beads may previously be suspended in a suitable solvent, in which the compound to be reacted with the magnetic beads has been suspended. Thereafter, in the subsequent operations or conservation step, light may preferably be shielded.

In the present invention, in order to allow a compound to come into contact with photoreactive compound-bound magnetic beads, any means that can be selected by persons skilled in the art may be used. For example, the magnetic beads suspended in a suitable solvent and the compound may be stirred at a moderate rate in a tube. Otherwise, the compound may be allowed to come into contact with the magnetic beads expended on the below-mentioned "support," so that the compound may be mixed with the magnetic beads on the support.

A solvent used in the preparation of a compound to be bound to magnetic beads can be selected, as appropriate, depending on the type of the compound to be bound thereto. For example, water, ethanol, methanol, acetonitrile, dimethyl sulfoxide, N,N-dimethylformamide, dioxane, chloroform, and the like can be used. The amount of a compound used to bind the above compound to the magnetic beads is different, depending on the type of the compound to be bound to the magnetic beads. For example, approximately 1 to 10 molecules of, preferably approximately 1 to 5 molecules of, and more preferably approximately 1 molecule of the compound is used with respect to 1 molecule of a photoreactive compound existing on the surface of each of the magnetic beads. Preferably, the number of molecules of the compound to be bound to the magnetic beads is slightly higher than that of the photoreactive compound existing on the surface of each of the magnetic beads. Otherwise, persons skilled in the art could readily determine the mixing ratio of the magnetic beads and the compound by carrying out preliminary experiments.

The present invention includes a step of extending magnetic beads on the surface of each of which a photoreactive compound has bound, together with a compound to be bound to the magnetic beads, on a support. The "support" used herein is not particularly limited. There can be used a support having a flat surface, which is made of a material that is not degenerated by irradiation with light such as UV (ultraviolet light), or by contacting with various compounds or solvents, and preferably a transparent material, and which does not affect the binding of the photoreactive compound to the compound and does not adsorb the magnetic beads, the photoreactive compound, and the compound. Examples of a preferred support include a glass, an earthenware, a ceramic, and a plastic. The form and area (area on which the magnetic beads and the like are extended) of such support are not particularly limited, and they can be selected, as appropriate, depending on the scale for carrying out the present invention (depending on the amount of the compound used, or the amounts of magnetic beads used, to which the compound is to be bound). For example, when the compound and the magnetic beads are used in small amounts, a slide glass, a glass petri dish (having, for example, a diameter of approximately 3 cm), or the like can be used.

The term "extend" is used herein to mean that magnetic beads are allowed to exist at a low density on a flat support. The magnetic beads may be suspended in a solution, or only the magnetic beads, containing no solution, may be in a dry state. When the magnetic beads are extended on a support, they are extended at a density as uniform as possible, and more preferably, they are extended to form a single layer. The density of the thus extended magnetic beads is, for example, $1 \times 10^8$ beads/cm$^2$ or less, preferably approximately $1 \times 10^3$ beads/cm$^2$ to $1 \times 10^8$ beads/cm$^2$, more preferably approximately $1 \times 10^6$ beads/cm$^2$ to $1 \times 10^7$ beads/cm$^2$, further preferably approximately $3 \times 10^6$ beads/cm$^2$ to $8 \times 10^6$ beads/cm$^2$, and further more preferably approximately $4 \times 10^6$ beads/cm$^2$ to $6 \times 10^6$ beads/cm$^2$.

Next, the present invention includes a step of applying light to the magnetic beads (to which the photoreactive compound has bound), which are extended together with the compound on the support, so as to form a covalent bond between the above-described photoreactive compound existing on the surface of each of the magnetic beads and the above-described compound. The light applied can be selected, as appropriate, depending on the type of the photoreactive compound used. There can be used light having a wavelength of, for example, 200 nm to 400 nm, and preferably around 360 nm. As a light source, a mercury lamp, laser light, light-emitting diode, and the like can be used, as appropriate. For example, a commercially available UV crosslinker may also be used. With regard to the intensity of the light applied, the time and the like, person skilled in the art can appropriately determine conditions suitable for the magnetic beads, photoreactive compound, and low-molecular-weight compound used, by carrying out preliminary experiments, etc. For example, when ultraviolet light is applied, if the density of the magnetic beads is set at $1 \times 10^8$ beads/cm$^2$ or less, the intensity of the ultraviolet light may be approximately 3 J/cm$^2$ to 6 J/cm$^2$ in total, and preferably 4 J/cm$^2$ in total. Moreover, if the intensity of the ultraviolet light applied is calculated relative to that applied to a single bead, it may be, for example, $4.0 \times 10^{-8}$ J or more. In a case in which such intensity is less than $4.0 \times 10^{-8}$ J, it may preferably be approximately $0.6 \times 10^{-8}$ J to $1.0 \times 10^{-8}$ J. It is to be noted that such ultraviolet light irradiation conditions (the intensity of the light and the irradiation time) can be increased or decreased, depending on a volume calculated from a bead diameter or the concentration of a magnetic substance contained in a bead substrate.

When light is applied to magnetic beads, the magnetic beads may be suspended in any given solvent. However, a dry state is preferable. When magnetic beads extended together with a compound on a support are dried, a drying method is not particularly limited. Any given drying method, which does not impair the reactivity of a photoreactive compound on the surface of each of the magnetic beads and does not affect the structure of the aforementioned compound and the like, can be applied. For example, under light shielding conditions, a solvent component is heated at an appropriate temperature of, for example, approximately 0° C. to 70° C., and preferably approximately 24° C. to 37° C., for an appropriate period of time, for example, for approximately 10 minutes to 1 hour, and preferably for approximately 30 minutes, so that the solvent component is evaporated. Thereafter, under light shielding conditions, the remaining magnetic beads may be dried for an appropriate period of time, for example, for approximately 10 minutes to 1 hour, and preferably for approximately 30 minutes, under reduced pressure, in which a vacuum pump or the like is used, as appropriate.

The magnetic beads that have been subjected to light irradiation are recovered by an adequate method. When light is applied to the dried magnetic beads, the surface of the support, on which the magnetic beads are attached, is rinsed with a suitable solvent, and the magnetic beads, together with the solvent, are then recovered into a suitable tube or the like.

This recovery step is repeated several times (for example, approximately 1 to 10 times, preferably approximately 2 to 8 times, and more preferably approximately 4 or 5 times), so that the rate of recovering the magnetic beads, to which the compound has bound, can be improved. The dried magnetic beads may strongly bind onto the support. Thus, it may be sometimes necessary to scratching off the attached magnetic beads from the surface of the support. In such a case, since the surface of the support is scratched by adding a certain level of physical force, a product that does not scrape off the surface of the support (for example, a chip, a scraper made of rubber, etc.) may be used.

Another embodiment of the present invention includes a method, in which the magnetic beads produced by the method of the present invention are used to select from an antibody library, a desired antibody reacting with a compound that has bound to the magnetic beads.

The type of the antibody library used in the present invention is not particularly limited, as long as it comprises a group of (several types of) antibodies. Examples of such antibody library may include: a molecular population having a molecular form of an immunoglobulin; a cell population presenting an antibody on the cell surface; and a virus presenting an antibody to a coat protein. Persons skilled in the art could readily select a library suitable for carrying out the present invention. An example of such library is a B cell population generating antibodies (for example, a DT40 cell population that is a cultured established B cell line derived from chicken, which is produced, for example, by an ADLib method (with regard to the details of the ADLib method, please see US20060183225; Seo et al, Nature Biotech. 23: 731-735, 200, for example)).

Examples of the antibody of the present invention include: antibodies having the form of an immunoglobulin; and all molecules which specifically bind to specific molecules and which are recognized as antibodies by persons skilled in the art, such as single-chain antibodies and fragments of immunoglobulin (e.g. Fv, F(ab')2, Fab, etc.). A method for selecting a desired antibody from an antibody library using the magnetic beads of the present invention is different depending on the antibody library used. Persons skilled in the art can readily determine selection conditions.

The embodiment of the present invention also includes a kit for producing the magnetic beads of the present invention. The kit of the present invention comprises, as appropriate, magnetic beads, a photoreactive compound, a compound to be bound to the magnetic beads, a buffer used for a method for producing the magnetic beads of the present invention, a magnet for recovering the magnetic beads, and the like. The magnetic beads comprised in the kit may be either magnetic beads to which the photoreactive compound has bound, or magnetic beads to which the photoreactive compound has not yet bound. Moreover, the magnetic beads comprised in the kit may be designed to prevent the dispersion of the beads in a suitable vessel or on a support (for example, the magnetic beads are fixed in a vessel by a magnet or the like), or the magnetic beads may be in a dry state or may be suspended in a solvent. Furthermore, instructions for use are included with the kit of the present invention. The instructions for use describe in detail a method for producing the magnetic beads of the present invention. The instructions for use included with the kit may be printed on a material such as a paper, or the instructions for use may also be an electrically or electromagnetically readable medium, such as a floppy (registered trademark) disk, CD-ROM, DVD-ROM, a Zip disk, a videotape, or an audiotape. Further, the instructions for use may be published on a website, which is designated by the manufacturer or distributor of the kit or informed via an electronic mail or the like. Thus, the instructions for use may not necessarily be included in the kit.

The present invention will be described more in detail in the following examples. However, these examples are not intended to limit the scope of the present invention.

EXAMPLES

Example

1. Experimental Method 1-1. Cell culture

DT40 cells derived from chicken B cells were cultured at 5° C. $CO_2$ at 39.5° C. in a $CO_2$ incubator. As a medium, Iscove's Modified Dulbecco's Medium (Invitrogen) was used. 10% FBS, 1% chicken serum, 100 units/mL penicillin, 100 µg/mL streptomycin, 55 µM 2-mercaptoethanol were added to the aforementioned medium, and the resultant medium was then used. In addition, Trichostatin A (Wako Pure Chemical Industries, Ltd.) dissolved in a concentration of 5 mg/mL in methanol was used as a stock, and it was then diluted with the aforementioned medium to a concentration of 2.5 ng/mL.

Jurkat cells (Riken BioResource Center) derived from human T-lymphocyte leukemia cells were cultured in an RPMI1640 medium (Invitrogen/GIBCO). To the medium, 10% fetal bovine serum (JRH Bioscience), 1 mM sodium pyruvate (Invitrogen/GIBCO), 100 units/mL penicillin, and 100 µg/mL streptomycin (Invitrogen/GIBCO) were added.

Human monocyte leukemia-derived THP-1 cells (ATCC) were cultured in an RPMI1640 medium (Invitrogen/GIBCO). To the medium, 10% fetal bovine serum (JRH Bioscience), 1 mM sodium pyruvate (Invitrogen/GIBCO), 100 units/mL penicillin, and 100 µg/mL streptomycin (Invitrogen/GIBCO) were added.

1-2 Immobilization of Photoreactive Crosslinker on Magnetic Beads

200 µL of a suspension (a density of magnetic beads=$4.0 \times 10^8$/mL) of magnetic beads (M450-Epoxy; Dynal) was collected into a 1.5-mL tube, and it was then left at rest on a magnet stand for approximately 2 minutes, so as to collect the magnetic beads. Thereafter, a supernatant was removed. 200 µL of buffer A (0.1 M $NaHCO_3$-dioxane (1:1)) was added to the residue, and the mixture was then suspended using a Vortex mixer. Thereafter, the suspension was left at rest on a magnet stand in the same above manner, and a supernatant was then removed. This washing operation was repeated 3 times in total, and the resultant was finally recovered in a precipitated state. N-(17-amino-3,6,9,12,15-pentaoxaheptadecacil)-4-(3-trifluoromethyl-3H-diazirin-yl)-b enzamide was dissolved in 200 µL of buffer A, and the obtained solution was then mixed with the above-described magnetic beads that were in a precipitated state, so that the magnetic beads were suspended in the solution.

Using a shaker (150 rpm/min), the mixture was reacted at 37° C. overnight under light shielding conditions. Thereafter, the resultant was washed with 200 µL of buffer A three times, and finally, 200 µL of a blocking solution (1 M ethanolamine, 0.1 M Tris-HCl, pH 8.0) was added to the resultant for suspension. Using a shaker (150 rpm/min), the obtained suspension was reacted at 37° C. for 2 hours under light shielding conditions. Thereafter, the reaction solution was washed with 200 µL of ethanol three times, with 200 µL of pure water two times, and with 200 µL of methanol two times. Thereafter, the magnetic beads were suspended in 200 µL of methanol.

1-3 Immobilization of Compound on Magnetic Beads

Figure 1A:
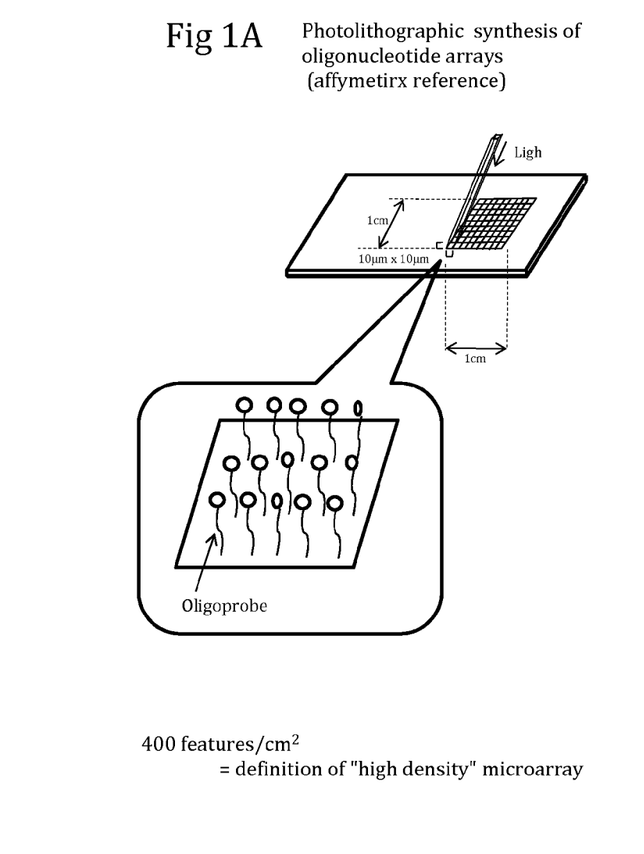
FIG. 1 is a conceptual view showing a process of binding a photoreactive compound to magnetic beads.
Figure 1B:
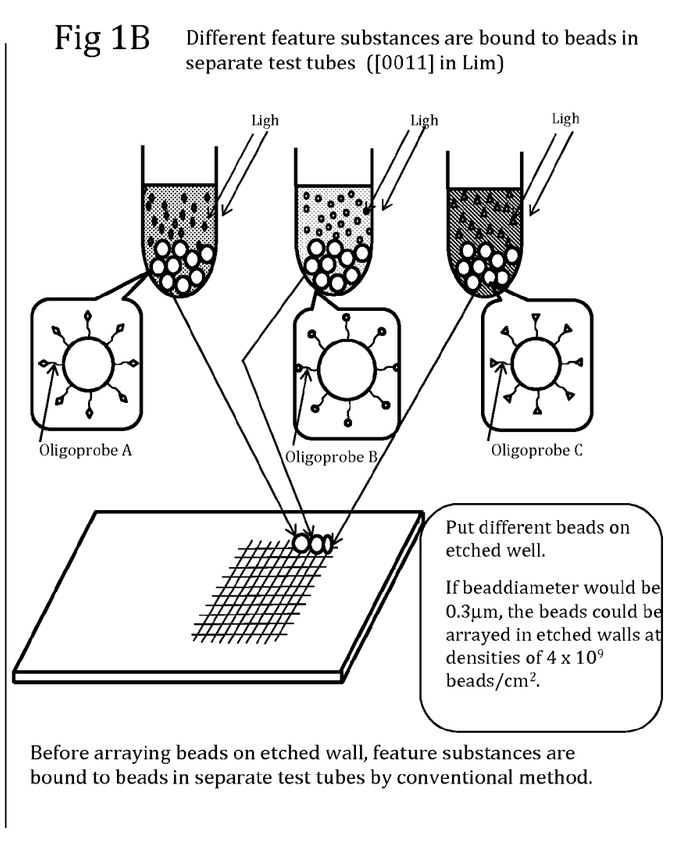

Approximately 100 μL (an amount of 50 μL to 150 μL was also applicable) of the above-produced suspension of magnetic beads each having a photoreactive compound (FIG. 1) was extended to a thin layer on a glass petri dish having a diameter of 3 cm (7.07 cm²) (in an amount of 7 μL, to 21 μL, and preferably approximately 14 μl per cm²). Any given low-molecular-weight organic compound was dissolved in 200 μL, of ethanol or methanol, and the obtained solution was gradually added dropwise onto the petri dish, on which the above-described suspension of magnetic beads had been extended. Thereafter, the reaction solution diffused in the petri dish was recovered with a pipette again, and it was then added dropwise to the central portion of the petri dish in a concentric state, so that it was extended on the petri dish again (wherein the final amount of the reaction solution became 21 μL, to 63 μL, and preferably approximately 42 μL).

This petri dish was placed on a 37° C. hot plate under light shielding conditions, and it was then heated for 30 minutes, so as to evaporate the solvent component. Furthermore, the residue was dried for 30 minutes under light shielding and reduced pressure conditions. Thereafter, using a UV crosslinker (DNA-FIX, 365 nm; manufactured by ATTO), ultraviolet light was applied to the resultant at an intensity of total 4 J/cm² (wherein an intensity of total 3 to 6 J/cm² was also applicable), and at an intensity of total $4 \times 10^{-8}$ J or more per single bead (wherein an intensity of total $0.6 \times 10^{-8}$ to $1.0 \times 10^{-8}$ J was also applicable). After completion of the ultraviolet light irradiation, 200 μL, of methanol was added to the petri dish, and the magnetic beads were then recovered such that the surface of the glass was scratched off with the tip of a Pipetman chip. The recovered suspension of magnetic beads was transferred into a 1.5-mL tube, and the tube was then left at rest on a stand with magnetism. In order to enhance the recovery rate, 200 μL, of methanol was further added to the petri dish. Thus, the residual magnetic beads were peeled, and they were then added to the 1.5-mL tube that had previously been left at rest on the stand. The tube was left at rest for approximately 2 minutes, so as to collect the magnetic beads, and 200 μL of methanol was recovered as a supernatant. The recovered methanol was added to the petri dish again, so as to further recover the residual magnetic beads. This operation was repeated five times. Thereafter, the magnetic beads recovered in a single 1.5-mL tube were washed with 200 μL of methanol ten times, and then with 200 μL of ethanol two times. Finally, the resultant was suspended in 200 μL of ethanol.

1-4. Selection of Antibody-Producing Cells

5 μL of the suspension of magnetic beads, to which the above-described antigenic compound had bound, was added to and mixed with 1 mL of a selection buffer (1% BSA-containing phosphate buffered saline PBS: 150 mM NaCl, 10 mM phosphate buffer, pH 7.4). The mixed solution was left at rest for 2 minutes on a magnet stand, and a supernatant was then removed. This operation was repeated three times, and finally, the resultant was suspended in 1 mL of a selection buffer, followed by cooling on ice. Thereafter, antibody-producing cells were screened in accordance with a standard ADLib method (see US20060183225; Seo et al., Nature Biotech. 23: 731-735, 2005, for example). Specifically, 100 mL of an ADLib cell library was recovered in two 50-mL tubes, and it was then centrifuged at 190×g for 10 minutes at 4° C. Thereafter, a supernatant was removed. Subsequently, the cells were suspended in 10 mL of a selection buffer, and the suspension was then transferred to a 15-mL tube. The suspension was centrifuged at 190×g for 10 minutes at 4° C., and a supernatant was then removed. The cells were suspended in 1 mL of a selection buffer, and the suspension was transferred to a 1.5-mL tube. The suspension was centrifuged at 1,100×g for 5 minutes at 4° C., and a supernatant was then removed. To this cell precipitate, 1 mL of the above-described suspension of antigen-bound magnetic beads that had been cooled on ice was added, and the magnetic beads were then suspended therein. Using a rotator, this suspension was reacted at 4° C. for 30 minutes, followed by suspension by pipetting. A tube was placed on a magnet stand, and the suspension was left at rest on ice for 5 minutes. Thereafter, a supernatant was removed, and the residue was then suspended in 1 mL of a selection buffer. The suspension was placed on a magnet stand again, and it was left at rest on ice for 3 minutes. This operation was repeated five times. Thereafter, the resultant was finally suspended in 0.5 mL of a selection buffer. 30 mL of a medium that had been heated to 37° C. was added to a reservoir manufactured by Corning, and the entire amount (0.5 mL) of the suspension was then added to the medium, followed by fully mixing by pipetting. Thereafter, this cell suspension was inoculated into each well of a 96-well plate in an amount of 300 μL/well. In this operation, 300 μL of medium alone was added as a background control to each of 7 wells. After that, it was cultured at 39.5° C. for 1 week in a $CO_2$ incubator.

1-5. ELISA

An antigen of interest and a control antigen were each diluted with ethanol, resulting in a concentration of 0.5 μg/mL or less. 100 μL of each antigen was added to a 96-well immunoplate, and it was then dried at 37° C. in a hybrioven, so as to produce an immunoplate. After drying, 200 μL of a selection buffer was added, and the mixture was then reacted at room temperature for 30 minutes or more. Thereafter, the reaction solution was washed with 200 μL of PBS three times. After completion of the washing operation, PBS was fully removed, and 100 μL each of culture supernatant was added to a target antigen (antigen of interest) well and a control (control antigen) well, followed by reaction at room temperature for 1 hour. Thereafter, PBS was removed, and the residue was washed with 200 μL of PBS five times. Subsequently, 100 μL of a solution obtained by diluting a secondary antibody (anti-Chicken IgM-HRP) by a factor of 10,000 with a selection buffer was added to each well, followed by reaction at room temperature for 45 minutes. Thereafter, the reaction solution was removed, and the residue was then washed with 200 μL of PBS five times. As much as possible amount of the residual solution was removed by suction. Finally, 100 μL of a 3,3',5,5'-tetramethylbenzidine (TMB) solution (DakoCytomation) was added to each lane every 5 seconds, and the mixture was then reacted at room temperature for 4 minutes. Thereafter, 100 μL of 20-fold diluted sulfuric acid (1 N) was added to each lane every 5 seconds, and the absorbance at 450 nm was then measured. It is to be noted that surfactants such as Tween must not be added to PBS and a selection buffer which are used for washing and reaction.

1-6. Co-Precipitation Experiment of Rapamycin-FKBP12 Complex Using Rapamycin-Bound Beads (1) The cultured Jurkat cells, derived from human T-lymphocyte leukemia cells, were recovered ($1 \times 10^6$/mL), and the thus recovered cells were then centrifuged at 1000 rpm for 10 minutes.

(2) After a supernatant had been removed, the residue was washed with PBS (137 mM NaCl, 3 mM KCl, 9 mM $NaHPO_4$, 1.5 mM $KH_2PO_4$, pH 7.4).

(3) The cells were suspended in 300 μL of Binding buffer (50 mL Tris-HCl, 150 mM NaCl, protease inhibitor cocktail, pH 7.5).

(4) The cells were disintegrated by an ultrasonic wave treatment, and the disintegration of the cells was then observed under a microscope.
(5) The disintegrated cell solution was centrifuged at 15000 rpm for 30 minutes at 4° C., and a supernatant was then recovered.
(6) The protein concentration in the cell extract of the supernatant was measured, and the extract was then diluted with Lysis buffer (137 mM NaCl, 3 mM KCl, 9 mM NaHPO$_4$, 1.5 mM KH$_2$PO$_4$, protease inhibitor cocktail, pH 7.4), resulting in a final protein concentration of 5 mg/mL.
(7) Subsequently, the obtained solution was mixed with 10-100 µL of the suspension rapamycin-bound beads produced by the above-mentioned method, and the mixed solution was then incubated at 4° C. for 30 minutes to 20 hours.
(8) Thereafter, the magnetic beads were collected using a magnet stand, and the supernatant was removed.
(9) The magnetic beads were washed with 1 ml of Wash buffer (Lysis buffer, 0.3% Triton X-100) five times.
(10) Finally, 15 µL of PBS and 15 µL of 2×SDS-PAGE sample buffer (125 mL Tris-HCl, 10% 2-mercaptoethanol, 4% SDS, 10% sucrose, pH 6.8) were added to the reaction solution, and the obtained mixture was then subjected to a heat treatment at 95° C. for 10 minutes.
(11) The magnetic beads were collected on a magnet stand, 10 µL of the supernatant was subjected to SDS-PAGE using 15% acrylamide gel, so as to separate a protein. Thereafter, Western blotting was carried out using an anti-FKBP1 antibody (Abeam, diluted by a factor of 1000).

1-7. Measurement of the Amount of TNF-α Released from THP-1 Cells (1) THP-1 cells were inoculated on a 24-well plate at a concentration of 6×10$^5$ cells per well.
(2) Lipolipids (LPS$_{0111}$, LPS$_{Re}$, and Lipid A; all of which were modified with magnetic beads according to the method of the present invention or were unmodified) were added, and the obtained mixture was then incubated at 37° C. for 4 hours.
(3) The cell culture solution was recovered into a 1.5-mL tube, a centrifugal operation (3,500 rotations, 4° C., 5 minutes) was then performed thereon, and a supernatant was then recovered. The amount of TNF-α contained in this supernatant was measured. The measurement was carried out in accordance with the protocols of Quantikine Human TNF-α/TNFSF1A manufactured by R & D Systems.
(4) 200 µL of the supernatant recovered in the method (3) above was added to an assay plate, to which 50 µL of Assay Diluent RD1F had previously been added, and the obtained mixture was then incubated at room temperature for 2 hours.
(5) The supernatant was decanted, and was then washed with 400 µL of Wash buffer four times.
(6) 200 µL of TNF-α Conjugate was added to the resultant, and the obtained mixture was then incubated at room temperature for 1 hour.
(7) The TNF-α Conjugate was decanted, and was then washed with 400 µL of Wash buffer four times.
(8) 200 µL of Substrate buffer was added to the resultant, and the obtained mixture was then incubated at room temperature under light shielding conditions for 20 minutes.
(9) 50 µL of Stop solution was added to the resultant, and the absorption spectrum at 450 nm was then measured.

Figure 2A:
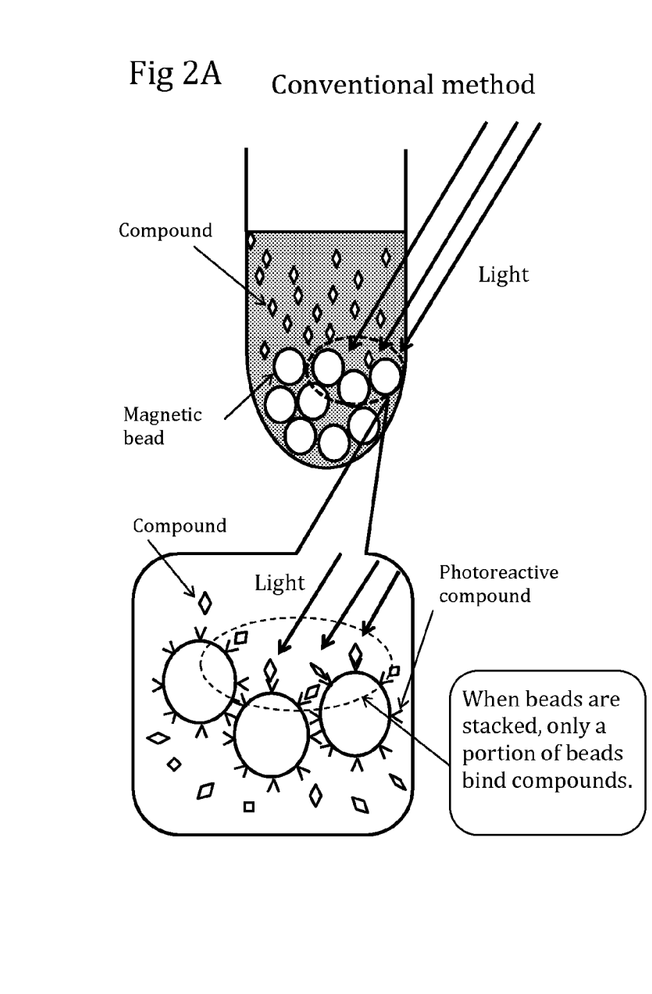
FIG. 2 shows the results obtained by selecting an antibody from an ADLib library, using cyclosporin A (CsA) bound to magnetic beads as an antigen.
Figure 2B:
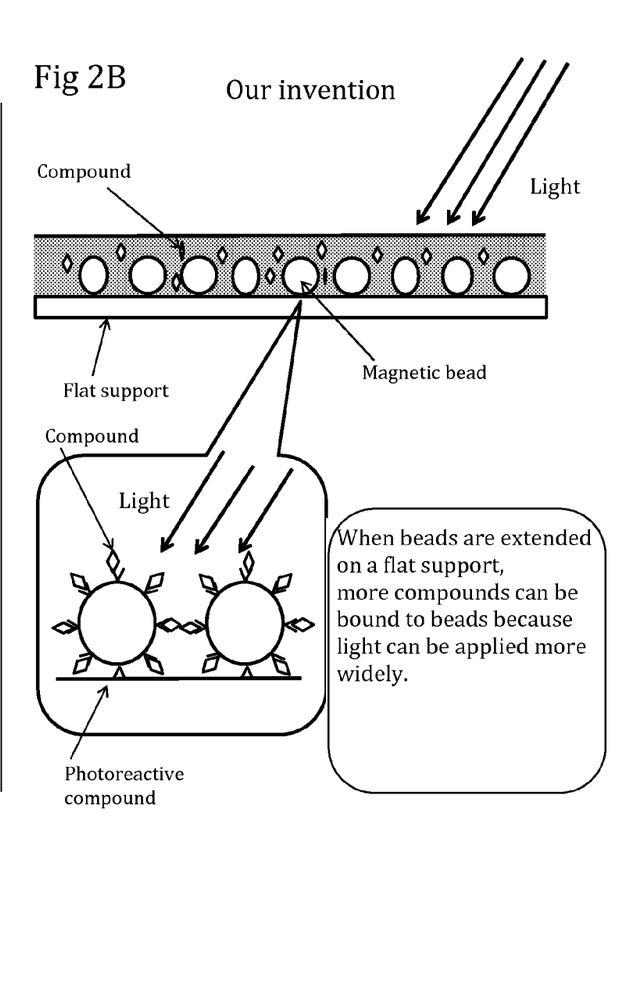

2. Results 2-1. Example regarding hydrophobic protein (cyclosporin A)
The above-described experiment was carried out using 0.5 µg of cyclosporin A. As a result, two types of clones, the O.D.450 value of which was 0.6 or more after completion of the ELISA, could be obtained (FIG. 2).

Figure 3:
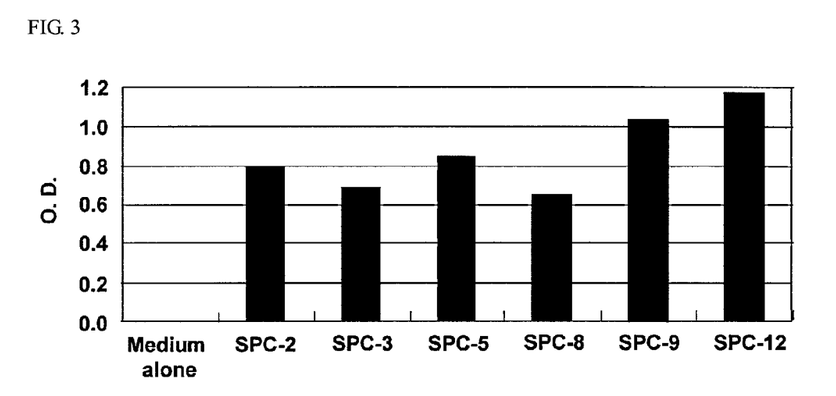
FIG. 3 shows the results obtained by selecting an antibody from an ADLib library, using sphingosylphosphorylcholine (SPC) bound to magnetic beads as an antigen.
Figure 4:
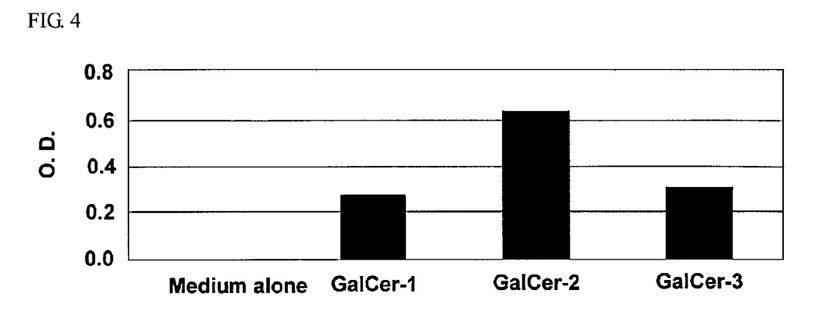
FIG. 4 shows the results obtained by selecting an antibody from an ADLib library, using sphingosine 1-phosphate (SIP) bound to magnetic beads as an antigen.
Figure 5:
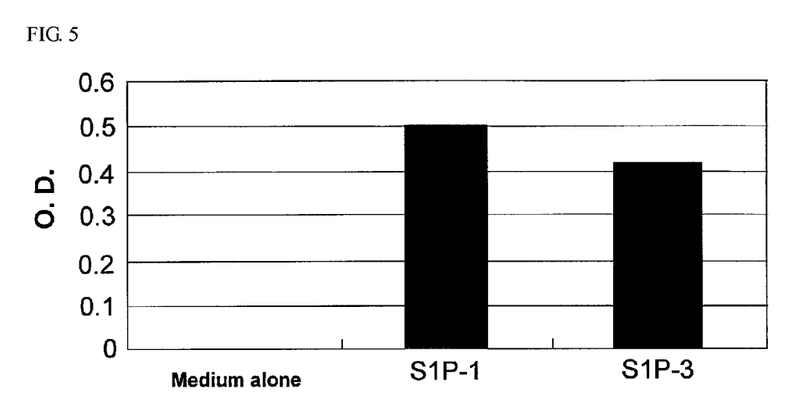
FIG. 5 shows the results obtained by selecting an antibody from an ADLib library, using galactosylceramide (GalCer) bound to magnetic beads as an antigen.

2-2. Example Regarding Lipids
Using glycolipids such as sphingosylphosphorylcholine (SPC) and galactosylceramide and sphingolipids such as sphingosine 1-phosphate (SIP) in an amount of 50 ng each, the above-described experiment was carried out. As a result, several types of cell clones producing a lipid antibody of interest, the O.D.450 value of which was 0.5 or more, could be obtained (FIGS. 3 to 5).

Figure 7:
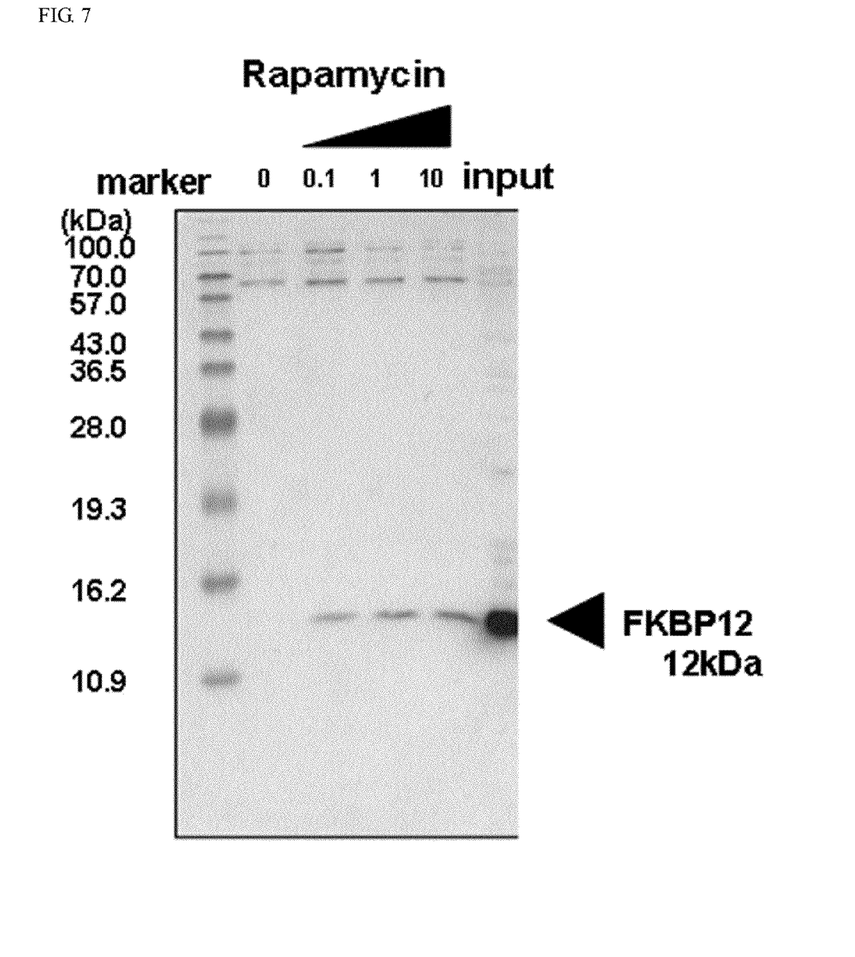
FIG. 7 shows the results of the co-precipitation experiment of FKBP12 using rapamycin-bound magnetic beads. The figure shows the results of Western blotting using an anti-human FKBP antibody. The term "input" represents the amount (mg) of rapamycin bound to the magnetic beads. The term "marker" represents a marker protein electrophoresed in the leftmost lane. The number written on the extreme left indicates a molecular weight.

2-3. Example Regarding Rapamycin-Bound Beads
Rapamycin (in different amounts of 0, 0.1, 1, and 10 mg) was allowed to bind to magnetic beads (100 µL; 4×10$^7$), and the rapamycin-bound magnetic beads were then incubated at 4° C. for 120 minutes in the extract of Jurkat cells (protein mass: 1.25 mg; concentration: 5 mg/mL). After completion of the incubation, using a mouse anti-human FKBP12 antibody (Abcam), Western blot analysis was carried out on the co-precipitate with the rapamycin-bound magnetic beads. As a result, it became clear that the amount of FKBP12 recovered together with the rapamycin-bound beads from the precipitate was increased in a bound rapamycin amount-dependent manner (FIG. 7). On the other hand, the amount of FKBP 12 recovered by a mock treatment (in a case in which the amount of rapamycin was 0 mg) was not detected.

From the above results, it became clear that rapamycin can be reliably and efficiently bound to magnetic beads according to the method of the present invention.

Figure 8:
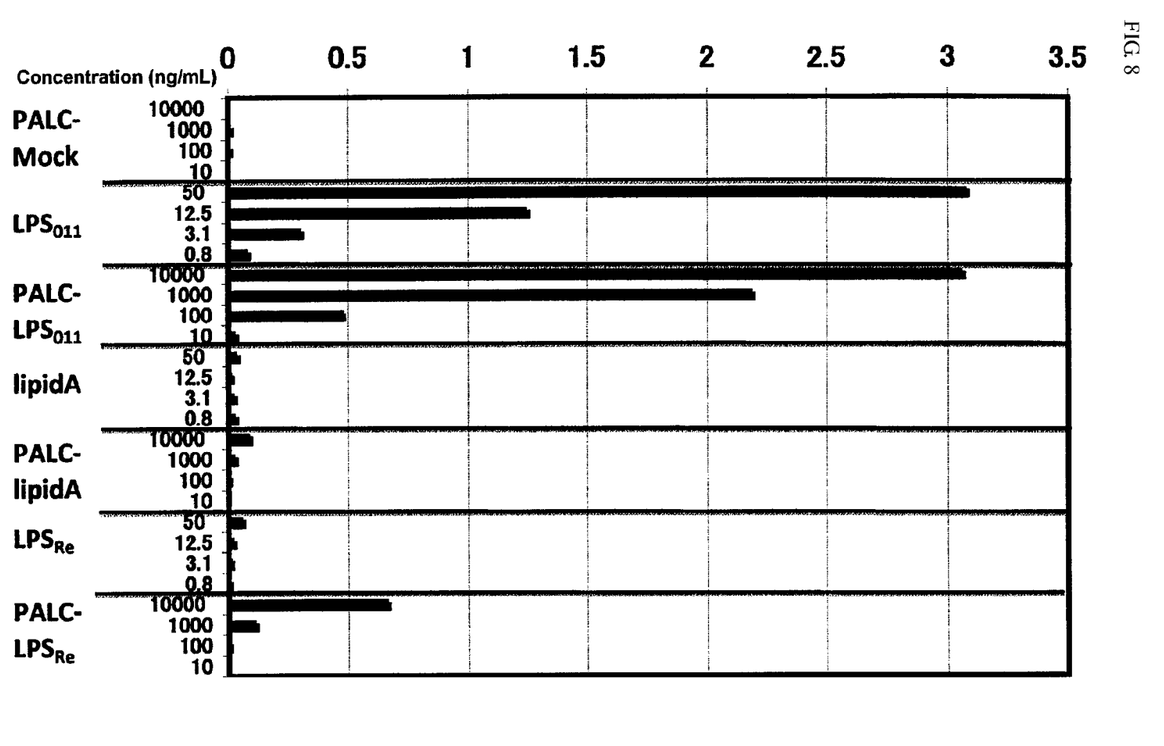
FIG. 8 shows the results obtained by measuring the amounts of TNF-α released from THP-1 cells, in which such release is induced by magnetic beads, to which various types of LPSs have bound. Magnetic beads-bound LPSs which had been produced according to the method of the present invention, and free LPSs, were each added in various concentrations shown in the figure to THP-1 cells, followed by incubation. Thereafter, the amounts of TNF-α released were indicated in a graph form. The amount of TNF-α released was shown as the absorbance at $OD_{450}$, using the kit manufactured by R & D Systems (please see experimental methods).

2-4. Studies Regarding Physiological Activity of Lps (Lipopolysaccharide)-Bound magnetic beads
Whether a lipolipid (LPS) that had been bound to magnetic beads according to the method of the present invention could retain an inflammatory signal-inducing physiological activity, was examined using THP-1 cells. Such inflammatory signal-inducing activity was examined by measuring the secretion of TNF-α from the cells (FIG. 8). From the results shown in FIG. 8, it is found that the LPS$_{011}$ immobilized on magnetic beads retains the activity of approximately ⅒ of that of free LPS$_{011}$. In addition, the responsiveness of Lipid A and LPS$_{Re}$ in the THP cells is not so high, but it could be confirmed that their magnetic beads-bound bodies have the activity of approximately ⅒ to 1/20 of their free bodies. It is to be noted that the concentration (ng/mL) of the magnetic beads-bound LPS group is only a value assumed from binding conditions, and thus, the actual value is assumed to be lower than the value shown in FIG. 8. From the above results, when a low-molecular-weight compound, such as LPS, immobilized on magnetic beads retains a physiological activity, magnetic beads, to a specific site of which the low-molecular-weight compound has bound, are collected in a living body by a magnetic force or the like, and such magnetic beads can be then used for the treatment of cancer and the like.

Comparative Example

Next, the compound (CsA) used as an antigen in [Example] was allowed to bind to magnetic beads by the conventional UV irradiation in a micro test tube, and an attempt was then made to select an antibody reacting with the compound (CsA). The results are shown below.

1. Experimental Method

DynaBeads, into which a photoaffinity linker had been introduced according to an ordinary method, and a methanol solution of cyclosporine A (CsA) were placed in a micro test tube, and they were then blended. After drying, UV was applied to the mixture, so that the CsA was immobilized on the beads (CsA beads). The CsA beads were recovered with methanol, and they were then washed by an ordinary method. In order to confirm that the CsA was immobilized on the beads, a protein competition binding experiment was carried out using the CsA beads and control beads produced by UV irradiation without mixing with the compound. In order to confirm CsA beads-binding specificity, a solution obtained by mixing magnetic beads-anti-CsA antibody and BSA at a ratio of 1:10 was added to each of the obtained CsA beads and control beads, so that they were reacted. Subsequently, the two types of beads were recovered by magnetic force, and were then washed several times. Thereafter, the protein bound to the beads was electrophoresed by SDS-PAGE.

2. Results

Figure 6:
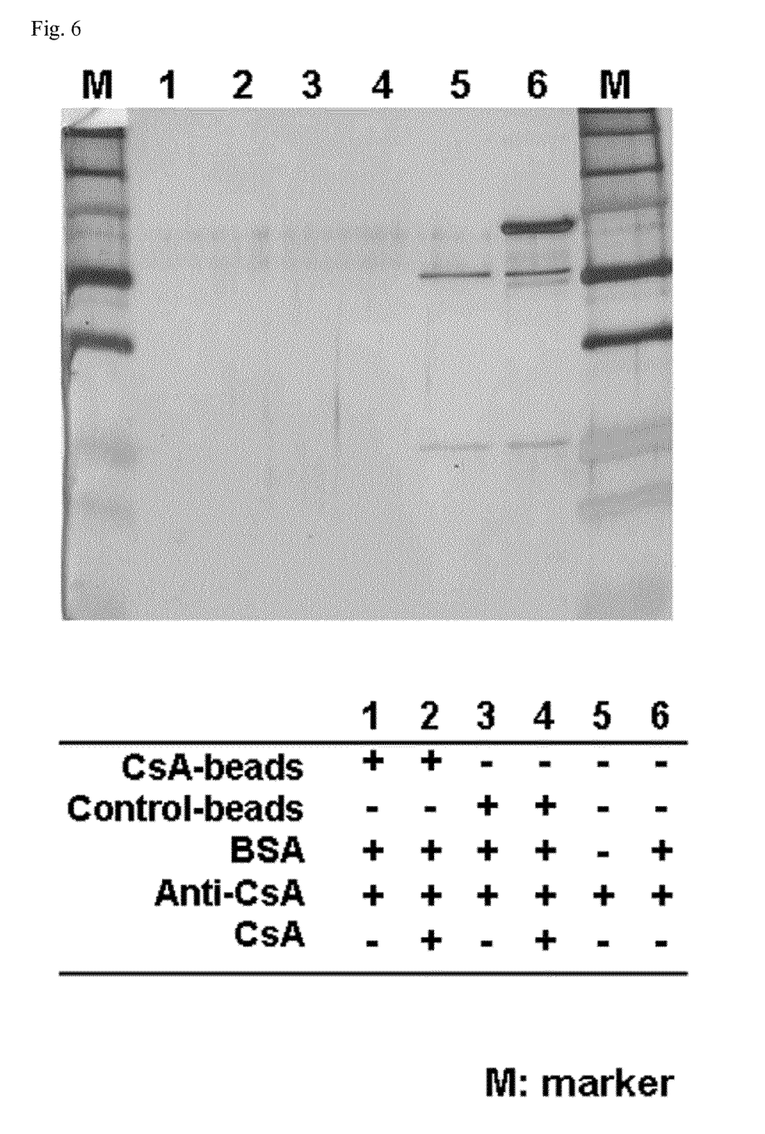
FIG. 6 shows the results obtained by binding a compound to magnetic beads according to the conventional method. Bound fractions: lanes 1 to 4; non-bound fractions: lanes 5 and 6.

FIG. 6 shows the results of the silver staining of SDS-PAGE. As is found from FIG. 6, the anti-CsA antibody did not bind at all to either the control beads or the CsA beads (see lanes 1 and 3 in FIG. 6).

From the above results, it is found that, according to the method of the present invention, it is possible to easily bind a compound to magnetic beads, although the compound is hardly bound to the magnetic beads by the conventional method, and that it becomes possible to effectively screen for an antibody reacting with the compound in any given antibody library.

INDUSTRIAL APPLICABILITY

According to the present invention, any given compound, and in particular, a compound having almost no amino groups can be stably and efficiently bound to magnetic beads. Accordingly, the present invention greatly contributes to the progression of technology in industrial fields associated with life science, such as technology in an antibody-associated field.

What is claimed is:

1. A method for producing compound-bound magnetic beads, which comprises:
   providing magnetic beads having a photoreactive compound bound on a surface thereof, wherein said photoreactive compound includes: a compound having an azido group; a compound having a diazo group or diazirine ring; a benzophenone, a conjugated ketone, an enone, an aromatic halogen compound or an olefin; a compound comprising a diazonium group; or N-(17-amino-3,6,9,12,15-pentaoxaheptadecacil)-4-(3-trifluoromethyl-3H-diazirin-yl)-benzamide;
   allowing a low molecular weight compound to come into contact with said magnetic beads;
   extending said magnetic beads together with said low molecular weight compound on a support; and
   applying light to said magnetic beads and said low molecular weight compound that are extended on said support to form a covalent bond between said photoreactive compound and said low molecular weight compound, wherein a density of said magnetic beads extended on said support upon application of light to said magnetic beads and said low molecular weight compound is not greater than $1 \times 10^8$ beads/cm$^2$.

2. The method according to claim 1, wherein said magnetic beads and said low molecular weight compound are dried, before applying said light thereto.

3. The method according to claim 1, wherein said low molecular weight compound has 0 to 5 amino groups.

4. The method according to claim 3, wherein said low molecular weight compound is a lipid.

5. A kit comprising said magnetic beads, said photoreactive compound, said low molecular weight compound, and an instruction manual, which is used to carry out the method according to claim 1.

6. A method for producing compound-bound magnetic beads comprising:
   providing magnetic beads including a photoreactive compound bound on a surface thereof, wherein said photoreactive compound includes: a compound having an azido group; a compound having a diazo group or diazirine ring; a benzophenone, a conjugated ketone, an enone, an aromatic halogen compound or an olefin; a compound comprising a diazonium group; or N-(17-amino-3,6,9,12,15-pentaoxaheptadecacil)-4-(3-trifluoromethyl-3H-diazirin-yl)-benzamide;
   allowing a lipid compound to come into contact with said magnetic beads, said lipid compound having 0 amino groups;
   extending said magnetic beads together with said lipid compound on a support;
   applying light to said magnetic beads and said lipid compound that are extended on said support to form a covalent bond between said photoreactive compound and said lipid compound, wherein a density of said magnetic beads extended on said support upon application of light to said magnetic beads and said lipid compound is not greater than $1 \times 10^8$ beads/cm$^2$;
   collecting said magnetic beads; and
   subjecting to an antibody library said collected magnetic beads, bonding an antibody from said antibody library to said lipid compound on said magnetic beads and using magnetism to select said magnetic beads having said bound antibody.

7. The method according to claim 1, wherein said low molecular weight compound has 0 amino groups.

8. The method according to claim 6 wherein said step of applying said light occurs while said magnetic beads are extended on said support as a single layer.

* * * * *

UNITED STATES PATENT AND TRADEMARK OFFICE
CERTIFICATE OF CORRECTION

PATENT NO.         : 8,901,044 B2                       Page 1 of 1
APPLICATION NO.    : 12/777562
DATED              : December 2, 2014
INVENTOR(S)        : Hiroyuki Osada et al.

It is certified that error appears in the above-identified patent and that said Letters Patent is hereby corrected as shown below:

On the Title Page:

Item (74), please delete "Pearre & Gordon LLP" and insert -- Pearne & Gordon LLP --

In the Specification:

Col. 11, line 30, please delete "Abeam" and insert -- Abcam --

Signed and Sealed this
Thirtieth Day of June, 2015

Michelle K. Lee
*Director of the United States Patent and Trademark Office*